(12) United States Patent
Maier et al.

(10) Patent No.: US 8,192,449 B2
(45) Date of Patent: Jun. 5, 2012

(54) NON-PENETRATING FIXING DEVICE

(75) Inventors: Christian Maier, Munich (DE); Georg Maier, Munich (DE)

(73) Assignee: Brainlab AG, Feldkirchen (DE)

( * ) Notice: Subject to any disclaimer, the term of this patent is extended or adjusted under 35 U.S.C. 154(b) by 1331 days.

(21) Appl. No.: 11/552,636

(22) Filed: Oct. 25, 2006

(65) Prior Publication Data

US 2007/0123916 A1    May 31, 2007

Related U.S. Application Data

(60) Provisional application No. 60/754,510, filed on Dec. 28, 2005.

(30) Foreign Application Priority Data

Oct. 25, 2005 (EP) ........................ 05023270

(51) Int. Cl.
*A61B 17/08* (2006.01)
(52) U.S. Cl. .................. 606/151; 606/86 R; 600/426
(58) Field of Classification Search ........... 606/53, 606/74, 151, 207, 86 R, 300–331; 600/426–429; 72/390.5; 7/125–137
See application file for complete search history.

(56) References Cited

U.S. PATENT DOCUMENTS

| 1,141,916 A * | 6/1915 | Aderer ............ 72/390.5 |
| 1,268,922 A * | 6/1918 | Bryan ............ 72/390.5 |
| 1,635,137 A * | 7/1927 | Mullens ............ 606/86 R |
| 1,985,108 A * | 12/1934 | Rush ............ 606/86 R |
| 2,291,413 A * | 7/1942 | Siebrandt ............ 606/103 |
| 2,362,957 A * | 11/1944 | Hackett ............ 606/86 R |
| 2,427,128 A * | 9/1947 | Ettinger ............ 606/86 R |
| 3,987,500 A | 10/1976 | Schlein |
| 4,009,712 A * | 3/1977 | Burstein et al. ............ 606/67 |
| 4,252,121 A | 2/1981 | Arnegger |
| 4,414,967 A | 11/1983 | Shapiro |
| 4,457,306 A * | 7/1984 | Borzone ............ 606/1 |
| 4,502,475 A * | 3/1985 | Weigle et al. ............ 606/105 |
| 4,587,916 A | 5/1986 | Guerette |
| 4,655,776 A | 4/1987 | Lesinski |
| 4,944,739 A * | 7/1990 | Torre ............ 606/53 |
| 4,944,743 A | 7/1990 | Gotzen et al. |
| 4,959,065 A | 9/1990 | Arnett et al. |
| 5,026,372 A | 6/1991 | Sturtzkopf et al. |
| 5,133,720 A | 7/1992 | Greenberg |
| 5,312,403 A * | 5/1994 | Frigg ............ 606/54 |
| 5,423,821 A | 6/1995 | Pasque |
| 5,536,271 A | 7/1996 | Daly et al. |
| 5,569,303 A | 10/1996 | Johnson |
| 5,674,221 A | 10/1997 | Hein et al. |
| 5,709,682 A * | 1/1998 | Medoff ............ 606/60 |

(Continued)

FOREIGN PATENT DOCUMENTS

DE    200 15 893 U 1    9/2000

*Primary Examiner* — Thomas C. Barrett
*Assistant Examiner* — Christopher Beccia
(74) *Attorney, Agent, or Firm* — Renner, Otto, Boisselle & Sklar, LLP

(57) ABSTRACT

A fixing device for securely fixing surgical equipment to a surgical field of a human or animal body includes a first lever element including a first gripping portion and a first handling portion, and a second lever element including a second gripping portion and a second handling portion. The and second lever elements can be connected such that they can be pivoted and detached with respect to each other.

14 Claims, 1 Drawing Sheet

U.S. PATENT DOCUMENTS

| | | | |
|---|---|---|---|
| 5,797,919 A * | 8/1998 | Brinson | 606/105 |
| 5,827,286 A | 10/1998 | Incavo et al. | |
| 5,945,548 A | 8/1999 | Duhamel et al. | |
| 6,102,912 A | 8/2000 | Cazin et al. | |
| 6,179,840 B1 | 1/2001 | Bowman | |
| 6,206,826 B1 | 3/2001 | Mathews | |
| 6,315,780 B1 * | 11/2001 | Lalonde | 606/86 R |
| 6,328,758 B1 | 12/2001 | Tornier et al. | |
| 6,364,884 B1 | 4/2002 | Bowman et al. | |
| 6,387,106 B1 * | 5/2002 | Howell et al. | 606/151 |
| 6,391,030 B1 | 5/2002 | Wagner et al. | |
| 6,447,517 B1 | 9/2002 | Bowman | |
| 6,461,358 B1 | 10/2002 | Faccioli et al. | |
| 6,540,770 B1 | 4/2003 | Tornier et al. | |
| 6,632,224 B2 | 10/2003 | Cachia et al. | |
| 6,679,888 B2 * | 1/2004 | Green et al. | 606/86 R |
| 6,685,706 B2 | 2/2004 | Padget et al. | |
| 6,685,708 B2 | 2/2004 | Monassevitch et al. | |
| 6,689,134 B2 | 2/2004 | Ralph et al. | |
| 6,730,086 B2 | 5/2004 | Hehli et al. | |
| 6,790,234 B1 | 9/2004 | Frankly et al. | |
| 6,827,723 B2 * | 12/2004 | Carson | 606/130 |
| 6,830,571 B2 | 12/2004 | Lenke et al. | |
| 6,835,197 B2 | 12/2004 | Roth et al. | |
| 6,856,828 B2 * | 2/2005 | Cossette et al. | 600/429 |
| 6,860,883 B2 | 3/2005 | Janowski et al. | |
| 6,910,890 B2 * | 6/2005 | Golden | 433/159 |
| 6,980,849 B2 * | 12/2005 | Sasso | 600/426 |
| 7,107,091 B2 * | 9/2006 | Jutras et al. | 600/429 |
| 7,189,244 B2 * | 3/2007 | Newton et al. | 606/105 |
| 7,473,257 B2 * | 1/2009 | Knopfle et al. | 606/101 |
| 7,497,029 B2 * | 3/2009 | Plassky et al. | 33/645 |
| 7,753,910 B2 * | 7/2010 | Ritland | 606/53 |
| 7,862,568 B2 * | 1/2011 | Vilsmeier et al. | 606/86 R |
| 2001/0053911 A1 * | 12/2001 | Hehli et al. | 606/53 |
| 2004/0019263 A1 * | 1/2004 | Jutras et al. | 600/407 |
| 2005/0149050 A1 * | 7/2005 | Stifter et al. | 606/102 |
| 2008/0027471 A1 * | 1/2008 | Hauri | 606/151 |

* cited by examiner

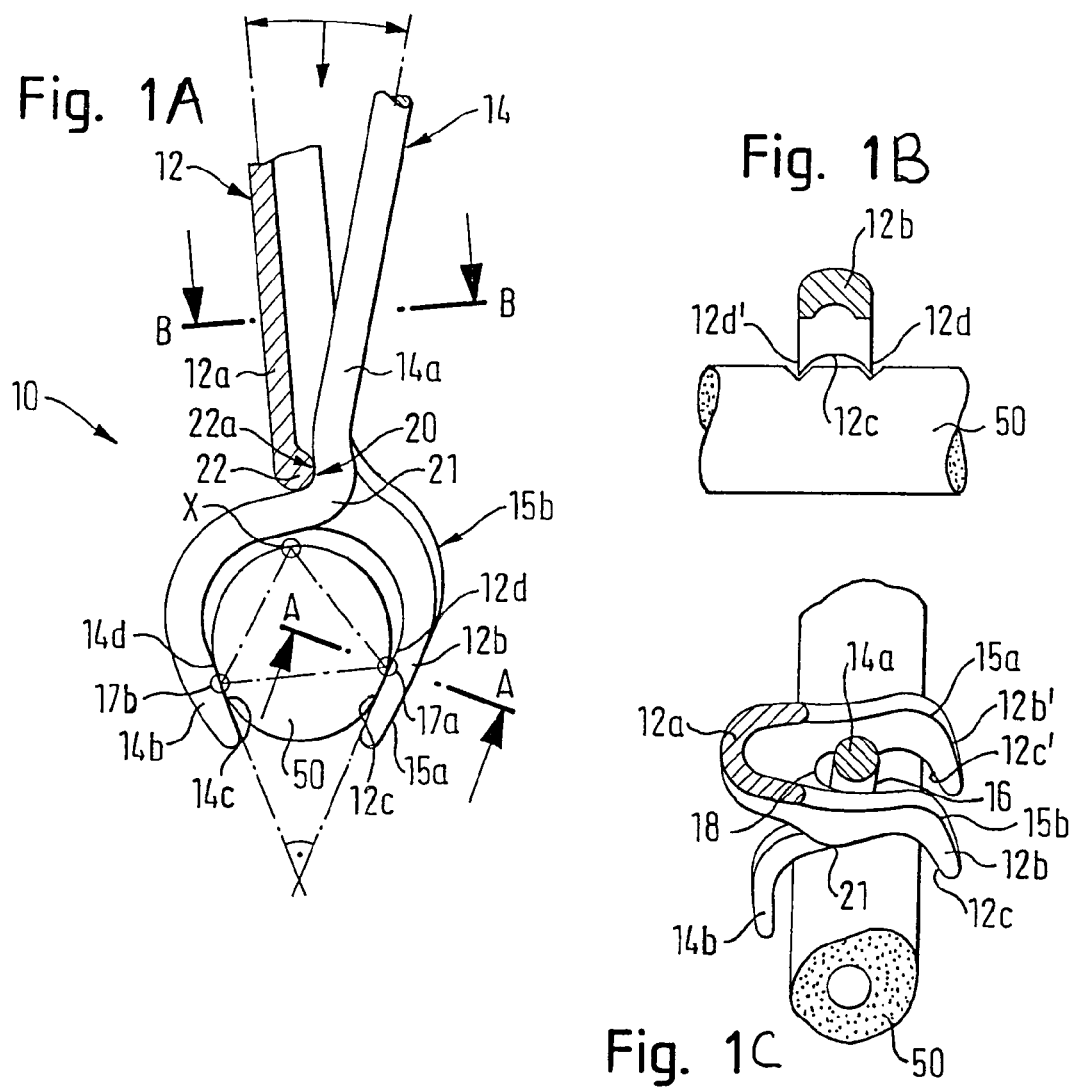
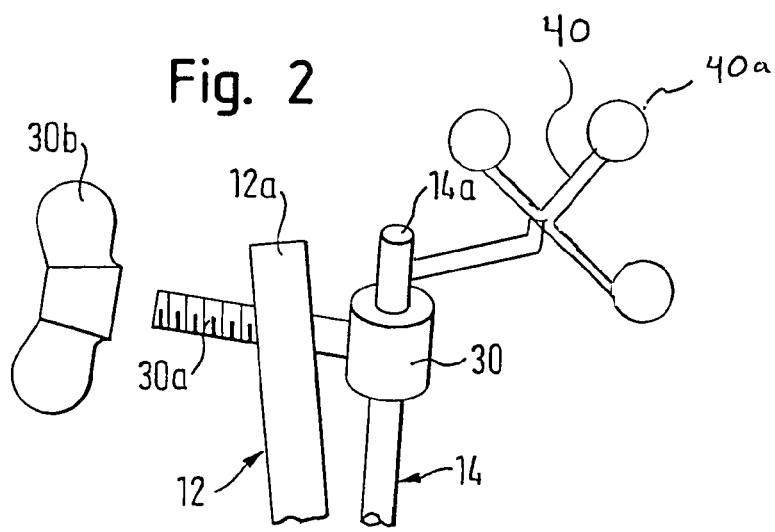

NON-PENETRATING FIXING DEVICE

RELATED APPLICATION DATA

This application claims priority of U.S. Provisional Application No. 60/754,510 filed on Dec. 28, 2005, which is incorporated herein by reference in its entirety.

FIELD OF THE INVENTION

The present invention relates to a device for securely fixing surgical equipment to a surgical field of a human or animal body, in particular a bone. Furthermore, the invention is related to a method for introducing a fixing device into a surgical field.

BACKGROUND OF THE INVENTION

Modern surgical procedures utilize improved accuracy to guarantee a minimally invasive operation, such that the patient is able to quickly recover from surgery. Therefore, surgical procedure are used that incur a minimal injury to the patient's body. To avoid injuring the patient's body during a surgical operation, the accuracy of the surgery is enhanced, and the surgery itself is performed so as to minimize entry into the body (which may not allow the surgeon to directly view the surgical field). In this scenario, it is nowadays common to use a reference element or reference array to provide a surgeon and/or a navigation system some points of orientation in the surgical field. To maintain the accuracy and the minimally invasive surgical technique, the reference element or reference array cannot be shifted, rotated or inaccurately located during surgery. Improperly locating the reference element or reference array may direct the surgeon away from the actual situation in the surgical field and can cause surgical errors.

Several different attachment methods are described in the prior art. In general, there are two groups of methods. One of these groups is directed to a bone attachment method according to which a bone is penetrated and a part of the fixing device is introduced into the bone. This group incurs the drawback that it is necessary to penetrate and thus injure a patient's body. In the other group, it is necessary to open a wide portal through the soft-tissue of a patient, in order to introduce a fixing device which needs significant space in order to enter and be fixed to a patient's bone. A list of publications directed to these two groups of methods is listed below.

| | |
|---|---|
| 6,860,883 | External Fixation Apparatus and Method |
| 6,835,197 | Bone Fixation System |
| 6,830,571 | Contourable Spinal Staple with Centralized and Unilateral Prongs |
| 6,790,234 | Reverse Shoulder Prosthesis System |
| 6,730,086 | Repositioning Instrument to Fixate Bone-fractures |
| 6,689,134 | Longitudinal Plate Assembly Having an Adjustable Length |
| 6,685,708 | Staples for Bone Fixation |
| 6,685,706 | Proximal Anchors for Bone Fixation System |
| 6,632,224 | Bone Fixation System |
| 6,540,770 | Reversible Fixation Device for Securing an Implant in Bone |
| 6,461,358 | Device for the External Fixation of Bones Fractures, in Particular Ankle Fractures |
| 6,447,517 | Instrument for Inserting Graft Fixation Device |
| 6,391,030 | Surgical Cable System and Method |
| 6,364,884 | Method of Securing a Graft Using a Graft Fixation Device |
| 6,328,758 | Suture Anchor with Reversible Expansion |
| 6,206,826 | Devices and Methods for Percutaneous Surgery |
| 6,179,840 | Graft Fixation Device and Method |
| 6,102,912 | Vertebral Rod of Constant Section for Spinal Osteosynthesis Instrumentations |
| 5,827,286 | Incrementally Adjustable Tibial Osteotomy Fixation Device and Method |
| 5,674,221 | External Fixator with Improved Clamp and Methods for Use |
| 5,569,303 | Apparatus and Method for Attaching an Object to Bone |
| 5,536,271 | Patella Reaming System |
| 5,423,821 | Sternal Closure Device |
| 5,133,720 | Surgical Drill Guide and Retractor |
| 5,026,372 | Fixation Device for the External Adjusting of Bone Fragments |
| 4,959,065 | Bone Plate with Positioning Member |
| 4,944,743 | Spinal Fixation Device |
| 4,655,776 | Prostheses for Ossicular Reconstruction |
| 4,587,916 | Device for Fixing the Wish-bone of the Sail-board to the Mast in a Fast and Rigid Manner |
| 4,414,967 | Internal Fixation of Bone, Tendon, and Ligaments |
| 4,252,121 | Separating Device |
| 3,987,500 | Surgically Implantable Total Ankle Prosthesis |

SUMMARY OF THE INVENTION

The present invention provides a fixing device and method that enables minimally invasive operating techniques. The present invention also provides a fixing device that can be fixed to a bone without penetrating and injuring the bone. The present invention further provides a fixing device that enables the surgeon to insert the fixing device through a small soft-tissue portal in the patient.

According to one aspect of the invention, a fixing device comprises a first lever element with a first gripping portion and a first handling portion; and a second lever element with a second gripping portion and a second handling portion, and wherein said first and second lever elements can be connected such that they can be pivoted and detached with respect to each other.

According to another aspect of the invention, a method of introducing the fixing device into a surgical field includes opening a soft-tissue portal in the patient; introducing one of first and second lever elements only into said portal; introducing the other of said first and the second lever elements into the portal; connecting the first and second lever elements to each other; and rotating the first and second lever elements with respect to a common rotational center to pivot first and second gripping portions towards each other and towards the surface of a bone to be gripped, wherein said first and said second lever elements can be connected such that they can be pivoted and detached with respect to each other.

Accordingly, one benefit of the present invention is that the fixing device can be fixed to a patient's bone without penetrating the bone tissue. Furthermore, it is possible to connect and detach elements of the fixing device such that they may be introduced into the patient's body through a comparatively small portal in the soft-tissue of the patient's body.

While a reference element or several reference elements or a reference array including several reference elements can be attached to the fixing device, it is also possible to fix other surgical equipment to the fixing device. For instance, it is possible to fix a probe, a lamp, an x-ray source or the like to the fixing device.

One of the first and second lever elements can include a receiving section and the other can include an insertion section. The insertion section can be removably introduced into the receiving section such that the insertion section may be pivoted with respect to the receiving section. This construction allows the fixing device to be assembled in the surgical field (e.g., in the patient's body), wherein the parts of the fixing device can be separately introduced and removed from the patient's body. When assembled within the surgical field, the parts can have the general shape of pliers.

The fixing device can include a securing element for securely maintaining an angle between the lever elements, in order to securely grip a bone. Accordingly, when a surgeon closes the lever elements of the device such that the bone is clamped between the gripping portions, the securing element can create and maintain an urging contact or force between the gripping elements and the bone. The securing element, for example, can be a screw or comparable component. This securing element can hold the levers together in their intended positions.

The receiving section can include a hole-like, groove-like or slit-like shape for receiving the insertion section or for guiding the insertion section into an operating position within the receiving section. The insertion section can be held and pivoted or rotated in the receiving section, in order to fix the device at a certain position on a bone.

The device can include at least one gripping surface on each of the first and second gripping portions. Providing special gripping surfaces enables the surgeon to securely fix the device on the bone. The gripping surfaces can have particular structures, for instance ridges, spikes or the like.

To allow the first lever element to pivot or rotate with respect to the second lever element, a guide surface can be formed on the first or second lever element. The other of the first and second lever element can be provided with a joint section having a sliding surface. The sliding surface cooperates with the guide surface to allow the pivoting or rotating movement. The joint section can be formed integrally with the other of the first and second lever elements.

The gripping surface or gripping surfaces can be broadened in a direction perpendicular to the main extension of the corresponding lever element and/or can be provided with at least one, preferably two extended edges directed towards the opposite gripping surface. This provides a further safety aspect that ensures the device cannot be displaced, rotated or the like, such that the reference elements or the reference array cannot be improperly positioned or located.

The fixing device described herein can be introduced into a surgical field by means of the following steps.

Firstly, a soft-tissue portal can be opened in a patient's body. The first and second lever elements then can be separately introduced, one after the other, through said portal. The first and second lever elements then can be connected with each other. The first and second lever elements then can be rotated or pivoted with respect to a common rotational center, in order to pivot the first and second gripping portions towards each other and towards the surface of a bone to be gripped, e.g., to be clamped between the gripping surfaces of the first and second lever elements.

It may be beneficial to ensure that the device is fixed to a bone such that at least three portions or three areas of the device are in direct contact with corresponding parts of the bone. This prevents the device from being rotated once it has been fixed to the bone.

Accordingly, the present invention enables a surgeon to attach a device and in particular a reference element or reference array to a surgical field, and in particular to a bone structure of a patient. Reference element or reference arrays are commonly used for image-guided surgery. The fixing device prevents translational and rotational displacements of the reference element or reference array or of any other surgical equipment which is fixed by means of the device. The device can be used in connection with computer aided and/or image guided surgical systems such as Vector Vision and/or Trauma 2.5, both well known products of the assignee of the present application.

Since the device does not need to penetrate a bone, the device does not block the volume of the bone. Thus, the device enables insertion of implants into the bone while the device is attached to the bone.

As stated above, the fixing device preferably comprises two levers. These levers can be formed such that the outer cortex of the bone fits the inner shape of the closed gripping surfaces of the levers. The levers may be assembled to form a plier-like surgical tool once they have been separately inserted through a soft-tissue portal in the patient. Accordingly, it is advantageous that the lever elements can be assembled by means of a combining element or joint element to allow the levers to be connected and to pivot or rotate, once introduced into the surgical field in order to form the plier-like instrument. For instance, a plug and a corresponding hole can be used to mount the lever elements. On the other hand, it is also possible to use a more complicated joint or combining element, comprising for instance a bolt which can be introduced into a bearing or the like, such that it can be rotated or pivoted. A hinge-like shape could also be used.

BRIEF DESCRIPTION OF THE DRAWINGS

The forgoing and other features of the invention are hereinafter discussed with reference to the drawings.

FIG. 1A is a fragmentary perspective view of an exemplary fixing device in accordance with the invention, wherein the levers are broken away in section.

FIG. 1B is a sectional view taken along the line A-A in FIG. 1A.

FIG. 1C is a fragmentary perspective cross-sectional view taken along the line B-B in FIG. 1A.

FIG. 2 illustrates an exemplary securing element in accordance with the invention that can be used in connection with the embodiment shown in FIG. 1A.

DETAILED DESCRIPTION

An exemplary fixing device according to FIG. 1A is indicated generally by reference indicator 10. Since the illustrated fixing device functions much like pliers to grip a body part, such as a bone, such fixing device is herein referred to as pliers. The skilled person will appreciate, however, that a fixing device according to the invention may take other forms as well.

The pliers 10 include a first lever element 12 and a second lever element 14 that are assembled to form the pliers 10. A surgeon's hand can grip the pliers at first and second handling portions 12a and 14a of the first and the second lever element 12 and 14. A bone 50 can be gripped or clamped by means of first gripping portion 14b of lever element 14 and second gripping portion as shown, the second gripping portion including two laterally spaced apart parts 12b and 12b'.

When introducing the elements of the pliers 10 into the surgical field in a patient's body, a surgeon may first introduce the second lever element 14 and then the first lever element 12, such that a knee portion 21 of the second lever element 14 approaches a guide surface 20 of the first lever element 12. Said knee portion 21 can be introduced through the guide surface between two fork-like or prong-like extensions 15a and 15b to form a secure connection between the first lever element 12 and the second lever element 14. At the end of the guide surface between the prong-shaped extensions 15a and 15b of the second gripping portion 12b and 12b', a sliding surface 20a can be provided that, once assembled, touches the guide surface 20 such that the two lever elements 12 and 14 can be rotated to urge areas of the first and second gripping portions 12b, 12b and 12b' against corresponding attachment points or attachment areas 17a and 17b with respect to the bone 50. To avoid a rotational movement of the levers and thus of the pliers 10 as a whole, the pliers can be attached to the bone 50 such that the pliers touch the bone at an additional support point or area X.

The first and second gripping portions 14b, 12b and 12b' can be provided with corresponding first and second gripping surfaces 14c, 12c and 12c'.

As shown in particular in FIG. 1B, the first and second gripping portions 14b, 12b and 12b' can be provided with the gripping surface 12c that can include a ridged or spiked structure or the like. Furthermore, extended edges 12d and 12d' can be provided at the edges of the corresponding gripping surfaces. The extended edges 12d and 12d' can be urged into the surface of the bone 50, such that the attachment of the pliers 10 to the bone can be made more secure against being displaced by a torque force or shifting force acting on the pliers 10.

As can be seen in FIG. 1A, the gripping area of the pliers 10 touches the bone 50 at three different points or areas X, 17a and 17b and, thus, minimizes the likelihood of the pliers 10 being displaced once fixed to a particular location on the bone.

FIG. 1C shows a situation immediately after inserting and assembling the levers and during the closing operation for urging the gripping surfaces 14c, 12c and 12c' against the surface of the bone 50.

Referring now to FIG. 2, the first lever element 12 can be provided with a U-shaped recess at its upper end. A securing element 30, and in particular a bushing or cylindrical bushing 30, the shape of which can depend on the cross-sectional shape of the second lever element 14, has been shifted over the upper end of the second lever element 14. A protrusion 30a (in the present case a threaded shaft) can be fixed to the bushing 30. The threaded shaft can extend through the U-shaped recess (not shown) in the upper end of the first lever element 12. A wing nut can be used as a fixing element 30b, to urge the first handling portion 12a in a rotational movement of the lever 12 towards the second handling portion 14a of the second lever element 14. Once tightened, the thumb nut 30b will securely hold the lever elements 12 and 14 in a particular position. A reference element 40, such as a reference star 40 including reflective markers 40a, for example, can be attached to the fixing device 10 via the first or second lever element 12 and 14.

Since it is possible to separately introduce the lever elements 12 and 14 into the patient's body and to assemble them therein, the fixing device or pliers 10 can be inserted and attached to a bone through a small soft-tissue portal in a patient. Furthermore, since it is possible to securely fix the pliers 10 to a bone without penetrating the bone tissue, the injury to the bone is very minor and the fixing device 10 allows other surgical instruments, implants or the like to be introduced, since the pliers 10 do not occupy much space within the bone.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A fixing device for securely fixing surgical equipment to a surgical field of a human or animal body, comprising:
   a first lever element including a first gripping portion, a first handling portion and an intermediate portion therebetween; and
   a second lever element including a second gripping portion, a second handling portion and an intermediate portion therebetween;
   wherein the intermediate portion of one of the first or second lever elements includes laterally spaced apart portions that are laterally spaced apart in a first direction and a pivot surface forming a pivot between the laterally spaced apart portions, the laterally spaced apart portions being laterally spaced apart sufficiently to receive therebetween the intermediate portion of the other of the first or second lever elements;
   wherein the laterally spaced apart portions form an aperture therebetween and are joined at one end of the aperture to form the pivot surface, the intermediate portion of the other lever element being movable into abutting engagement with the pivot surface and to pivot against the pivot surface for relative rotation of the lever elements about an axis parallel to the first direction; and
   wherein the aperture extends from the pivot surface a distance that allows for insertion of the gripping portion of the other lever element between the laterally spaced portions, whereby the first and second lever elements can be pivoted and detached with respect to one another.

2. The fixing device according to claim 1, wherein the aperture has a hole-like, groove-like or slit-like shape for guiding said other of the first or second lever elements into an operating position within the intermediate portions.

3. The fixing device according to claim 1, further comprising a securing element for securely maintaining an angle between the lever elements or securely urging said gripping portions against a bone.

4. The fixing device according to claim 3, wherein the aperture has a hole-like, groove-like or slit-like shape for guiding said other of the first or second lever elements into an operating position within the intermediate portions.

5. The fixing device according to claim 4, wherein at least one of the gripping portions is broadened in a direction perpendicular to the handling portion of the corresponding lever element.

6. The fixing device according to claim 1, wherein each of said first and second gripping portions has at least one gripping surface.

7. The fixing device according to claim 6, wherein the gripping surface of at least one of the gripping portions is broadened in a direction perpendicular to the handling portion of the corresponding lever element.

8. The fixing device according to claim 1, wherein the first and second lever elements are formed to provide a plier-like instrument.

9. The fixing device according to claim 8, wherein at least one of the gripping portions is broadened in a direction perpendicular to the handling portion of the corresponding lever element.

10. The fixing device according to claim 1, further comprising a reference element or reference array on at least one of the lever elements for tracking a position of the fixing device in three dimensional space.

11. The fixing device according to claim 1, wherein the intermediate portions are formed by prong-like extensions.

12. The fixing device according to claim 4, wherein at least one of the gripping portions is provided with at least one extended edge directed towards the opposite gripping portion.

13. The fixing device according to claim 6, wherein the gripping surface of at least one of the gripping portions is provided with at least one extended edge directed towards the opposite gripping surface.

14. The fixing device according to claim 8, wherein at least one of the gripping portions is provided with at least one extended edge directed towards the opposite gripping portion.

* * * * *